United States Patent
Rajendran et al.

(10) Patent No.: US 7,060,308 B2
(45) Date of Patent: Jun. 13, 2006

(54) *CARALLUMA* EXTRACT PRODUCTS AND PROCESSES FOR MAKING THE SAME (76) Inventors: Ramaswamy Rajendran, No. 5, BDA Domlur II Stage, III Phase, Bangalore-560 071, Karnataka (IN); Kamala Rajendran, No. 5, BDA Domlur II Stage, III Phase, Bangalore-560 071, Karnataka (IN)

( * ) Notice: Subject to any disclaimer, the term of this patent is extended or adjusted under 35 U.S.C. 154(b) by 0 days.

(21) Appl. No.: 10/837,613

(22) Filed: May 4, 2004

(65) Prior Publication Data

US 2004/0247702 A1    Dec. 9, 2004

(30) Foreign Application Priority Data

Jun. 4, 2003   (IN) ........................ 451/MAS/2003

(51) Int. Cl.
*A61K 35/78*   (2006.01)
(52) U.S. Cl. ..................................... 424/725
(58) Field of Classification Search ................ 424/724, 424/725
See application file for complete search history.

(56) References Cited

U.S. PATENT DOCUMENTS 6,376,657 B1   4/2002   Van Heerden et al.
6,703,051 B1   3/2004   Bates et al.

OTHER PUBLICATIONS

Ahmed, M.M. et al., "Anti-inflammatory activity of *Caralluma tuberculata* alcholic extract," Nov. 20, 1992, FITOTERAPIA, vol. LXIV, No. 4, 1993.*
Rizwani, G.H. et al., "Biological Efficacy of the extracts and constituents of *Caralluma tuberculata* and *C. edulis*," J. Fac. Pharm. Gazi, 11(1), 43-53, (1994).*
Zakaria, M.N.M. et al., "Anti-nociceptive and anti-inflammatory properties of *Caralluma arabica*," Journal of Ethnopharmacology, 76 (2001) pp. 155-158.*
M.N.M.Zakaria et al., "Evaluation of aintinociceptive and anti-inflammatory properties of *Caralluma arabica*", Pharm. Pharmacol., vol. 51 (Supplement), p. 117 (1999).

(Continued)

*Primary Examiner*—Susan Coe
*Assistant Examiner*—S B. McCormic-Ewoldt
(74) *Attorney, Agent, or Firm*—Robert E. Bushnell, Esq.

(57) ABSTRACT

A *Caralluma* extract and a method of making thereof which can be standardized and reproducible, and which prevents the glycosides from decomposition, which can reduce the undesirable non-glycoside components. In the first *Caralluma* extract, the resinous material does not exceed 0.5% by weight, and, in the second *Caralluma* extract, the resinous material does not exceed 1.0% by weight. The first extract is produced by optionally pretreatment of plant materials, optional crushing and/or grinding, extraction, and concentration. The filtration step and the resin removal step may be performed optionally. The second extract is produced by contacting the first *Caralluma* extract with excipients, drying, powdering, sifting and blending. The *Caralluma* extracts of the present invention can be used for medical purposes and as food additives.

71 Claims, 4 Drawing Sheets

OTHER PUBLICATIONS

M. N. M. Zakaria et al.; "Anti-nociceptive and anti-inflammatory properties of *Caralluma arabica*"; Journal of Ethnopharmacology, 76 (2001), 155-158.

M. Kamil et al.; "Identification and quantification of flavonoids from *Caralluma arabica* and its quality control studies"; J. Pharm. Pharmacol., 1999, 5: (Supplement), 225.

R. Radhakrishnan et al.; "Antihyperglycaemic effects of *Caralluma arabica* in diabetic mice"; © J. Pharm. Pharmacol., 1999, 5 (Supplement), 116.

M. N. M. Zakaria et al.; "Evaluation of antinociceptive and anti-inflammatory properties of *Caralluma arabica*"; J. Pharm. Pharmacol., 1999, 5 (Supplement), 117.

* cited by examiner

CARALLUMA EXTRACT PRODUCTS AND PROCESSES FOR MAKING THE SAME

CLAIM OF PRIORITY

This application makes reference to, incorporates the same herein, and claims all benefits accruing under 35 U.S.C. §119 from applications for CARALLUMA EXTRACT PRODUCTS AND PROCESSES FOR MAKING THE SAME and for TREATMENT AND MANAGEMENT OF OBESITY AND OBESITY RELATED DISORDERS/SYMPTOMS USING CARALLUMA EXTRACTS earlier filed in the Indian Patent Office on 4 Jun. 2003 and 27 Apr. 2004 and thereby duly assigned Serial Nos. 451/MAS/2003 and 384/CHE/2004, respectively.

BACKGROUND TO THE INVENTION

1. Field of the Invention

This invention relates to *Caralluma* extract, more particularly, to *Caralluma* extract products and to processes for making the same.

2. Description of the Related Art

The *Caralluma* group of plants belongs to the Asclepiadaceae family and comprises a number of species that are distributed throughout the world. Some of these species include but are not limited to: *c. indica, c. fimbriata, c. attenuata, c. tuberculata, c. edulis, c. adscendens, c. stalagmifera, c. umbellata, c. penicillata, c. russeliana, c. retrospiciens, c. arabica* and *c. lasiantha*. Some of the species are distributed throughout various parts of India.

*Caralluma* plants are small, erect and fleshy. They have 4 grooved stems that are almost round in shape. They are generally devoid of leaves and form small flowers in a variety of dark colors. Their pods are erect, linear and about 2.5 cms in length and feel velvety to the touch. The thorns of *Caralluma* are soft. The species of *Caralluma* found in India are edible and form part of the traditional medicine system of the country.

The medicinal properties of *Caralluma* includes carminative, febrifugal, anthelmintic, anti-rheumatic, anti-diabetic and anti-hyperglycaemic, anti-pyretic, anti-inflammatory, anti-nociceptive, and anti-oxidant effects. The *Caralluma* extracts have been also found to be appetite-suppressants as well as CNS stimulants.

The medicinal properties of *Caralluma* have been attributed to the glycosides contained therein. A glycoside is a condensation product obtained from a sugar and non-sugar compound and may have further components such as ring structures that are substituted or non-substituted. The glycosides contained in *Caralluma* belong to the pregnane group of glycosides. Some of the pregnane group of glycosides found in *Caralluma* plants include, but are not limited to:

i. caratuberside A,
ii. caratuberside B,
iii. bouceroside I,
iv. bouceroside II,
v. bouceroside III,
vi. bouceroside IV,
vii. bouceroside V,
viii. bouceroside VI,
ix. bouceroside VII,
x. bouceroside VIII,
xi. bouceroside IX, and
xii. bouceroside X.

Another important property of *Caralluma* glycosides is their surprising synergy. This synergy was first observed by the present inventors. The synergy is exhibited by pairs of *Caralluma* glycosides and by higher order combinations, although the synergy contributed by the higher order combinations is not of much significance, in view of the fact that the content of glycosides other than the above-mentioned two, namely, caratuberside and bouceroside in *Caralluma* is extremely small. The caratuberside-bouceroside synergy is therefore, only one of the synergies found in *Caralluma* glycosides. The synergies found in *Caralluma* glycosides include the synergy arising out of isomer—isomer interactions in the two glycosides. The synergy is particularly strong with respect to the following three physiological effects of the glycosides: a reduction of body weight and treatment of obesity in subjects; a reduction of blood glucose in subjects and a reduction or elimination of arthritic and other joint pains. The uses of *Caralluma* for these physiological effects and the method of treatment thereof using *Caralluma* was first studied and investigated by the present inventors. The present inventors are also the first to study the related subject of the increase of muscle mass in subjects by use of *Caralluma* and the method of treatment for the same using *Caralluma*.

An interesting fact first observed by the present inventors is that the maximum caratuberside-bouceroside synergy is found when the caratuberside-bouceroside ratio is substantially equal to the CB ratio found in *c. indica*. Three other species, namely, *fimbriata, attenuate* and *tuberculata* have substantially the same ratio value and substantially the same glycoside content as *c. indica*. These four species are referred to hereinafter as Group I *Caralluma* species. Four more species, namely, *stalagmifera, umbellata, lasiantha* and *edulis* also have substantially the same CB ratio but somewhat lesser total content of glycosides than the Group I species. The latter four species are referred to hereinafter as Group II species and the caratuberside-bouceroside ratio is referred to as the CB ratio, or the CBR for short.

The prior art provides a process for extraction of *Caralluma* wherein the aerial parts of *Caralluma* plants are extracted by means of 10% aq. ethanol. The prior art process has a number of drawbacks and furthermore results in only a crude extract product that is not standardized, that is non-reproducible and that is not representative of the original plant material from which it is extracted. These drawbacks of the prior art product and process are described further hereinbelow.

In the first reference (M. N. M. Zakaria, M. W. Islam, R. Radhakrishnan, H. B. Chan, M. Kamil, A. N. Gifri, K. Chan, A. Al-Attas, J. of Ethnophamacology, 76 (2001), 155–158), *c. arabica*, a *Caralluma* species found in West Asia, was extracted using 10% aq. ethanol. The aerial parts of the plant were dried in the shade, powdered and then extracted with 10% aq. ethanol. The solvent was removed from the extract by evaporation under vacuum at 40° C. using a rotary evaporator. The dried extract was re-suspended in distilled water and the slurry used for a pharmacological investigation to establish the anti-nociceptive and anti-inflammatory properties of *c. arabica* with respect to mice and rats.

In the second reference (M. Kamil, A. F. Jayaraj, F. Ahmed, C. Gunasekhar, S. Samuel, K. Chan, M. Habibullah, J. Pham. Pharmacol. 1999, 5: (Supplement), 225), powdered *c. arabica* plant material was extracted using 10% aq. ethanol in a soxhlet extractor for eight hours. The flavone glycosides, luteolin-4'-O-nehesperidoside and kaempferol-7-O-nehesperidoside were isolated from the extract and the concentrations thereof in *c. Arabica* determined.

In the third reference (R. Radhakrishnan, M. N. M. Zakaria, M. W. Islam, X. M. Liu, K. Chan, M. Habibulah, J. Pham. Pharmacol., 1999, 5 (Supplement), 116.) and the fourth reference (M. N. M. Zakaria, M. W. Islam, R. Radhakrishnan, H. B. Chan, A. Ismail, K. Chan, M. Habibulah, J. Pharm. Pharmacol. 1999, 5 (Supplement), 117), the aerial parts of *c. arabica* are stated to have been extracted by means of 10% ethanol. No further details of the adopted process are disclosed.

The first drawback among the drawbacks of the prior art process is that decomposition of the *Caralluma* glycosides occurs during processing. This fact was not recognized by the prior art and was first observed by the present inventors. When a *Caralluma* extract (solution) is concentrated by evaporation of solvent therein, charring and overheating of material occurs at higher concentrations. The overheating/charring causes the decomposition despite the provision of considerable agitation.

The charring/overheating is primarily caused by the high viscosities of the *Caralluma* extracts of high concentrations. The high viscosities are caused by the presence of the resinous matter of *Caralluma* plants that get extracted out in the extract along with the glycosides. The present inventors observe that under certain conditions of extraction considerable quantities of the resins are extracted out along with the glycosides.

The decomposition was observed first by the present inventors both in the concentration step and in the extraction step. Where the extraction temperature is held at levels higher than 75° C., thermal decomposition of the glycosides occurs. Such high temperatures enhance the viscosity of the extract and increase the risk of decomposition in the concentration step.

In a soxhlet type apparatus, because of the column effect, the *Caralluma* plant matter would come into contact with solvent vapors that have a much greater ethanol content than 10% that is used to charge the apparatus. The extraction temperature would also remain generally above 75° C. Under these conditions, the present inventors have observed that considerable decomposition occurs and furthermore large quantities of the resinous matter in *Caralluma* plant matter get extracted out into the extract.

The process conditions are not fully disclosed in the third and fourth references but it is fair to assume that the extracts are evaporated to dryness to obtain the product in a solid form suitable for pharmacological studies. Thus, the decomposition must certainly occur in the method adopted by the third and fourth references.

The second drawback of the prior art process is that the non-glycoside components in *Caralluma* are extracted. The non-glycoside components are tannins, pectins and the resinous matter and others. The present inventors have found that at low ethanol concentrations considerable quantities of tannins and pectins are extracted out with the glycosides while at high concentrations the resins go preferentially into solution. These inventors observe that, when 10% aq. ethanol is used, an extract contains considerable percentage of the tannins and pectins. So, in the process conditions adopted in the first, third and fourth references, the *Caralluma* extract obtained would have considerable impurities in the form of tannins and pectins that have a deleterious effect on the shelf life of the glycoside product. In the second reference, ethanol concentrations of over 80% are likely to be encountered by the *Caralluma* plant matter in the soxhlet apparatus. The present inventors have found that the extract under these conditions would contain high amounts of the *Caralluma* resins.

The third drawback of prior art is that the *Caralluma* extract product obtained by the prior art process is non-standard in so far as the composition thereof would vary from one extraction to another. It is unrepresentative in so far as it would not reflect fully either the various constituents of *Caralluma* glycosides or their relative proportions that are found in the original plant matter. Further, as the composition would vary from extract to extract the *Caralluma* extract product of the prior art process cannot be considered to be reproducible.

Apart from the pharmacological studies of a few of the medicinal aspects of *Caralluma*, the prior art does not provide for any concrete medical applications of *Caralluma*. The present inventors have pioneered such applications. The applications would require *Caralluma* constituents in various forms such as tablets, injectables and others which would have to be made from a suitable intermediate that contains the principles of *Caralluma*. Such an intermediate that contains the principles of *Caralluma* and that could be the starting point is neither known or defined in the prior art.

In summary, the drawbacks of the prior art process include, but are not limited to:

i. non-standardized, non-representative and non-reproducible product;

ii. process conditions conducive to the decomposition of the glycosides;

iii. the extraction of undesirable non-glycoside components of *Caralluma* into the extracts, such as the tannins, pectins and resins that would affect the purity and storage properties of the product and that have side effects on the subjects treated with *Caralluma* glycoside products;

iv. no provision for removal of the undesirable non-glycoside components from the extracts in the process of prior art; and v. process parameters not optimized from the point of view of process economics or from the point of view of obtaining the desirable *Caralluma* intermediate product(s).

SUMMARY OF THE INVENTION

It is an object of this invention to eliminate the above-mentioned drawbacks and to define one or more suitable *Caralluma* extract products that are standardized, representative of the *Caralluma* plant material from which they are derived, are reproducible and which form suitable starting materials (intermediates) for the medicinal products of *Caralluma* or food additives.

It is another object of the present invention to provide an improved liquid type *Caralluma* extract.

It is yet another object of the present invention to provide an improved solid type *Caralluma* extract.

It is still yet another object of the present invention to provide an improved method for making the *Caralluma* extract in view of the extraction costs.

It is further another object of this invention to provide processes for making the *Caralluma* extract products wherein the decomposition is minimized or eliminated; wherein the extraction of the undesirable non-glycoside components along with the glycosides is minimized and wherein purification is provided for removal of the undesirable components.

It is still another object of the invention to optimize the specifications of the suitable *Caralluma* extract products and the process in the best interests of the economics of the process and the requirements of the applications of *Caralluma*.

It is a further object of this invention to maintain substantially the same CBR in the *Caralluma* extract products as found in the Group I and II *Caralluma* species in view of the presence of the synergy.

In order to achieve the above and other objectives, the preferred process for making a first embodiment of a *Caralluma* extract from *Caralluma* plants comprising the steps of:

i. pre-treatment of the *Caralluma* plant material by one or more optional operation such as washing, cleaning, soaking, drying, cutting, chopping, blanching, and others, if and as necessary;

ii. crushing and/or grinding of the plant material obtained from step (i), if, and to the extent, desired;

iii. extracting the material obtained from step (ii) in one or more stages by means of a suitable solvent/solvent mixture and/or with a solution obtained from another extraction, the nature of the solvent/solvent mixture and the concentration thereof and the temperature of extraction being selected such as to minimize or substantially prevent the extraction of the resinous matter therein;

iv. concentrating the extract batch(es)(solutions) obtained from step (iii) either singly or as mixtures of one or more thereof in a first concentration stage and further optionally in a second concentration stage by removal of the solvent/solvent mixture by any of known means such as the evaporation of the solvent/solvent mixture to yield the *Caralluma* extract, the solvent/solvent mixture being recovered, if desired;

v. optionally returning one or more of the extract batch(es) or parts thereof before the first concentration stage to step (iii) for contacting with the plant material to be extracted, the batch(es) being subjected optionally to filtration so as to remove particulate solid matter, if any; and vi. optionally subjecting the material-in-process to a resin extracting operation by means of a resin dissolving solvent as part of the step (i), or immediately following the steps (i) or (ii) or (iii) or immediately after the first concentration stage.

The *Caralluma* extract made according to the above method is a first *Caralluma* extract product, and may include 5% to 15% w/w pregnane glycoside or above 15% w/w pregnane glycoside according to the user's needs. The first *Caralluma* extract includes preferably not more than 0.5% W/W resinous matter, and is preferably a liquid type.

In order to achieve the above and other objectives, the preferred process for making a second embodiment of a *Caralluma* extract, comprising the steps of:

i. pre-treatment of the *Caralluma* plant material by one or more optional operations such as washing, cleaning, soaking, drying, cutting, chopping, blanching, and others, if and as necessary;

ii. crushing and/or grinding of the plant material obtained from step (i), if, and to the extent, desired;

iii. extracting the material obtained from step (ii) in one or more stages by means of a suitable solvent/solvent mixture and/or with a solution obtained from another extraction, the nature of the solvent/solvent mixture and the concentration thereof and the temperature of extraction being selected in order to minimize or substantially prevent the extraction of the resinous mater therein;

iv. concentrating the extract batch(es)(solutions) obtained from step (iii) either singly or as mixtures of one or more thereof in a first concentration stage and further optionally in a second concentration stage by removal of the solvent/solvent mixture by any of known means such as the evaporation of the solvent/solvent mixture to yield the first *Caralluma* extract, the solvent/solvent mixture being recovered, if desired;

v. optionally returning one or more of the extract batch(es) or parts thereof before the first concentration stage to step (iii) for contacting with the plant material to be extracted, the batch(es) being subjected optionally to filtration so as to remove particulate solid matter, if any;

vi. optionally subjecting the material-in-process to a resin extracting operation by means of a resin dissolving solvent as part of the step (i), or immediately following the steps (i) or (ii) or (iii) or immediately after the first concentration stage;

vii. contacting the first *Caralluma* extract with a suitable excipient and further with a suitable binder as necessary, and subjecting the materials to a mixing/blending operation;

viii. drying the material obtained from step (vii) by any of the known methods;

ix. powdering the material obtained from step (viii) if required and to the size required by any one of the known methods of milling; and x. sifting the milled material of step (ix) and subsequently blending the sifted material to yield the second *Caralluma* extract.

The *Caralluma* extract made according to the above method is a second *Caralluma* extract, and may include 25% to 30% w/w pregnane glycoside or above 30% w/w pregnane glycoside according to the user's needs. The *Caralluma* extract includes preferably not more than 1% w/w resinous matter, and is preferably a solid type.

The *Caralluma* extract made according to the above methods may be used in medicines having at least one of, but not limited to, the following pharmacological effects: carminative, febrifugal, anthelmintic, anti-rheumatic, anti-diabetic and anti-hyperglycaemic, anti-pyretic, anti-inflammatory, anti-nociceptive and anti-oxidant.

BRIEF DESCRIPTION OF THE DRAWINGS

A more complete appreciation of the invention, and may of the attendant advantages, thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

In this specification, depending on the context the term 'extraction' refers either to the process of extraction as a whole or to the individual step of extraction (leaching) that forms a part of the process. In the individual step of extraction, *Caralluma* plants, or parts thereof, are contacted with a suitable solvent that extracts out (leaches out) one or more constituents/components thereof. Similarly, the term 'extract' refers, depending on the context, either to the solution that is obtained during, and/or at the end of the extraction step, or to the solid mass that would be obtained upon removal by evaporation or otherwise, of the solvent contained in the solution. The solid mass is also sometimes referred to herein as the 'solute', which has also been used herein to refer to the one or more components of *Caralluma* that are soluble in the solvent. The soluble components may be desired ones from the point of view of extraction or otherwise.

In this specification, the term "solvent" includes solvent mixtures unless the context requires otherwise, that is, the expression 'solvent/solvent mixture' has been shortened to 'solvent' in the interests of clarity and conciseness.

In this specification, the terms '*Caralluma* plant material' or 'plant material' or 'plant matter' refer to the raw material at the commencement of the process, the 'plant material' at various stages of processing in the processes of the invention being referred to as 'material-in-process'. However, for the sake of clarity and conciseness the term 'plant material' or 'plant matter' is also used to refer to the 'material-in-process' at various stages of the process.

The "first *Caralluma* extract" product (or the *Caralluma* extract, Technical) refers to a product that is designed to be a suitable starting material, intermediate, for a number of pharmaceutical products containing the principles of *Caralluma*, or a liquid product. The first *Caralluma* extract may contain one or more or all the glycosides of *Caralluma*. Similarly, the proportions of the glycosides therein may have any set of values. Preferably, the product contains at least both the major pregnane glycosides of *Caralluma*, namely, caratuberside and bouceroside. Further, it is preferred that the proportion of the two major glycosides is substantially the same as the proportions found in the *Caralluma* species of the Groups I and II. That is, the CBR, the ratio of caratuberside and bouceroside therein is preferably 9:1 to 11:1. Further, it is also preferred that the resin content in the first *Caralluma* extract product does not exceed 0.5% by wt.

The second *Caralluma* extract (or the Standardized *Caralluma* extract) of the invention refers to a product that is further processed from the first *Caralluma* extract. The second *Caralluma* extract is designed to be a suitable starting material (intermediate) for several pharmaceutical products containing the principles of *Caralluma*. The second *Caralluma* extract contains the glycosides of *Caralluma* and may contain one, more or all of the glycosides within the scope of the invention. Similarly, the glycosides may be in any relative proportion. Preferably, the extract contains both the pregnane *Caralluma* glycosides, namely, caratuberside and bouceroside and preferably they are substantially in the proportions as found in *Caralluma* species of the Group 1 and II, that is, a CBR of 9:1 to 11:1. Preferably the resin content in the second *Caralluma* extract does not exceed 1.0% by wt.

The present invention and, particularly, the term "*Caralluma* extract" or "*Caralluma* plant material" means that the extract or the material is from any species of *Caralluma* group even if this specification does not list all the species of *Caralluma* group.

Typical composition of the first *Caralluma* extract product of the invention of the two preferred concentrations are given below.

TABLE 1

The first *Caralluma* extract
(from Group I Species)

| Test parameter | Specification |
| --- | --- |
| Appearance | brown to dark brown liquid |
| Solubility in water | soluble |
| Total dissolved solids | 65% minimum w/w |
| Total Bitters | 1.5% minimum w/w |
| Total Saponin Glycosides | 5% minimum w/w |
| Total pregnane glycosides | Above 15% w/w |
| Resinous matter | not more than 0.5% w/w |
| Total microbial count | 5,000 cfu/gm. maximum |
| *E. coli* and *salmonella* | absent |
| Coliforms | absent |
| *P. aeruginosa* | absent |
| *S. aureus* | absent |
| Heavy metals | 10 ppm maximum |

TABLE 2

The first *Caralluma* extract
(from Group II Species)

| Test parameter | Specification |
| --- | --- |
| Appearance | brown to dark brown liquid |
| Solubility in water | soluble |
| Total dissolved solids | 65% minimum w/w |
| Total Bitters | 0.5% minimum w/w |
| Total Saponin glycosides | 2% minimum w/w |
| Total pregnane glycosides | 5%–15% w/w |
| Resinous matter | not more than 0.5% w/w |
| Total microbial count | 5,000 cfu/gm. maximum |
| *E. coli* and *salmonella* | absent |
| Coliforms | absent |
| *P. aeruginosa* | absent |
| *S. aureus* | absent |
| Heavy metals | 10 ppm maximum |

The processes according to the present invention can provide any desired concentration of the glycosides in the products by suitable operation of the extraction and concentration steps and of the other steps. The two preferred concentration ranges of the first *Caralluma* extract are by way of example, that is, by way of preferred embodiments and should not limit the scope of the invention.

It is preferred to make the *Caralluma* extract containing substantially all the glycosides of *Caralluma*, the desired CBR, low non-glycoside components such as tannins, pectins and resinous matter.

The glycoside content of the second *Caralluma* extract may have any value according to the present invention. After considering the process economics including the costs of extraction, and the desirable specification of the Extract for downstream processes, and the glycoside contents of the Group I and II species, the present invention has arrived at two preferred concentrations of the second embodiment of the *Caralluma* extract, namely, a pregnane glycoside content of over 30% and from 25% to 30%. The two glycoside contents are the specifications obtained by extracting the Group I and II species, respectively, using the processes of the inventions in a generally optimized manner.

The second *Caralluma* extract of the invention preferably comprises the *Caralluma* glycosides adsorbed on an excipient and is in the powder form. The preferred composition of The second *Caralluma* extract is given in Tables 3 and 4.

TABLE 3

The second *Caralluma* extract
(from Group I *Caralluma* species)

| Test parameter | Specification |
| --- | --- |
| Appearance | brown to dark brown powder |
| Solubility in water | 75% minimum w/w |
| Loss on drying | 10% maximum w/w |
| Total Bitters | 3% minimum w/w |
| Total saponin glycosides | 10% to 30% w/w |
| Total pregnane glycosides | above 30% w/w |
| Resinous matters | Not more than 1% w/w |
| Total microbial count | 5,000 cfu/gram maximum |
| *E. coli* and *salmonella* | absent |
| Coliforms | absent |
| *P. aeruginosa* | absent |
| *S. aureus* | absent |
| Heavy metals | 10 ppm maximum |

TABLE 4

The second *Caralluma* extract
(from Group II *Caralluma* species)

| Test parameter | Specification |
| --- | --- |
| Appearance | brown to dark brown powder |
| Solubility in water | 75% maximum w/w |
| Loss on drying | 10% maximum w/w |
| Total bitters | 1% minimum w/w |
| Total saponin glycosides | 3% to 5% w/w |
| Total pregnane glycosides | 25%–30% w/w |
| Resinous matters | not more than 1% w/w |
| Total microbial count | 5,000 cfu/gm. maximum |
| *E. coli* and *salmonella* | absent |
| Coliforms | absent |
| *P. aeruginosa* | absent |
| *S. aureus* | absent |
| Heavy metals | 10 ppm. Maximum |

The purpose of the excipient is to adsorb the *Caralluma* glycosides thereon and further to provide an extended surface area for rapid and substantially complete removal of the traces of water, the extraction solvent and the resin dissolving solvent if used. Any of the known excipients can be used. The preferred excipients are maltodextrin and magnesium carbonate.

Figure 1:
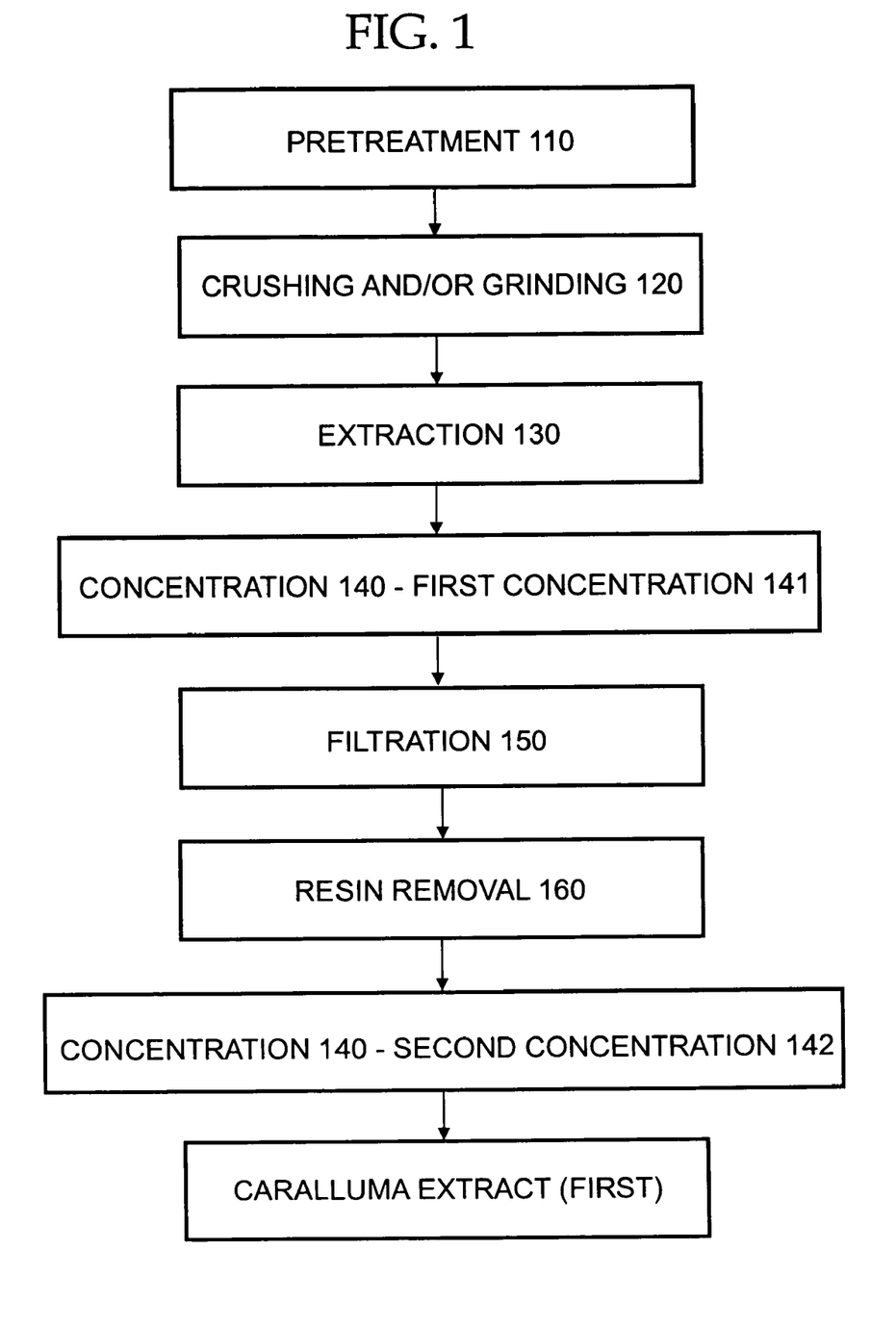
FIG. 1 shows an example of the process for making the first *Caralluma* extract from *Caralluma* plant matter.
Figure 2:
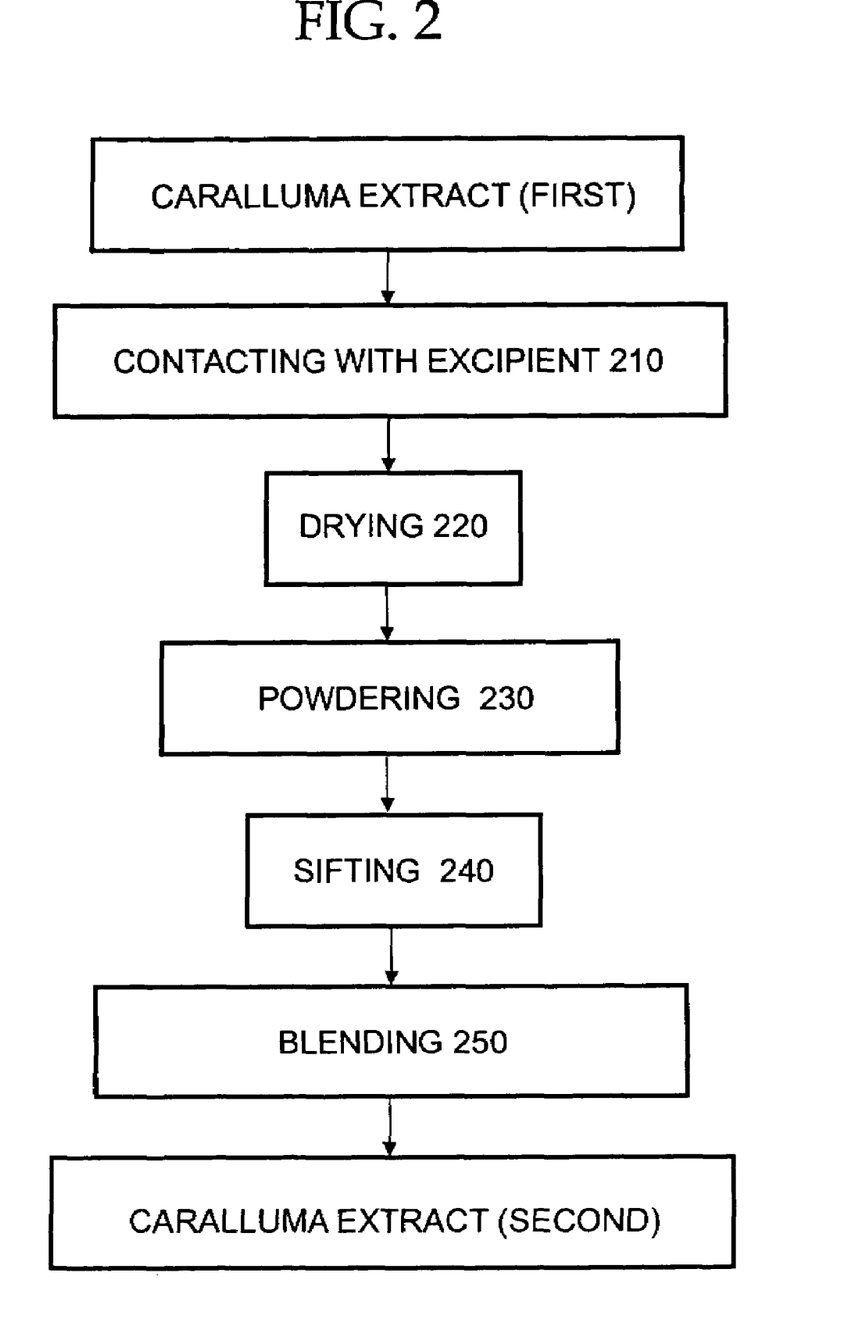
FIG. 2 shows an example of the process for making the second *Caralluma* extract from the first *Caralluma* extract.
Figure 3:
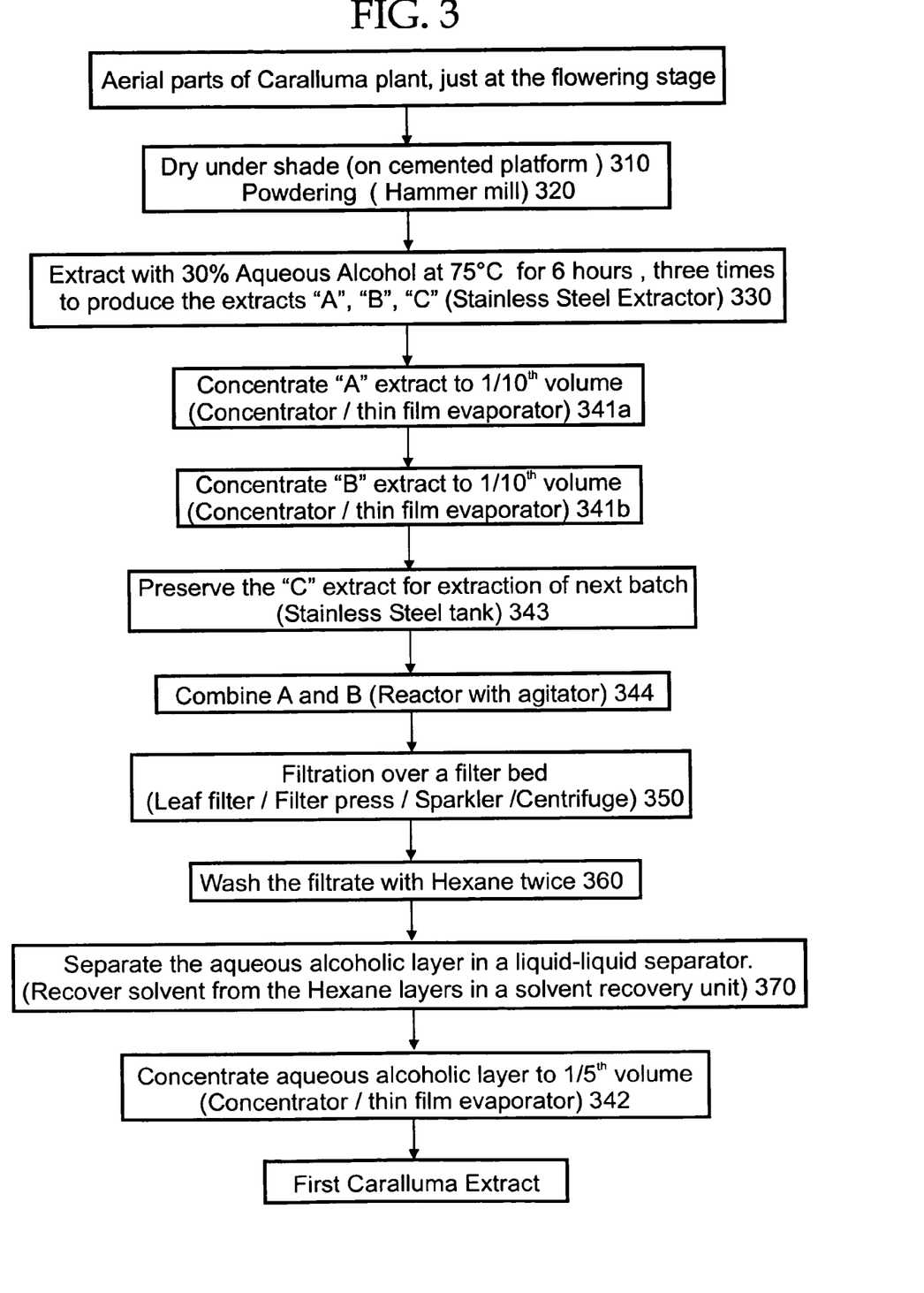
FIG. 3 shows one of the preferred processes for making the first *Caralluma* extract from *Caralluma* plant matter.
Figure 4:
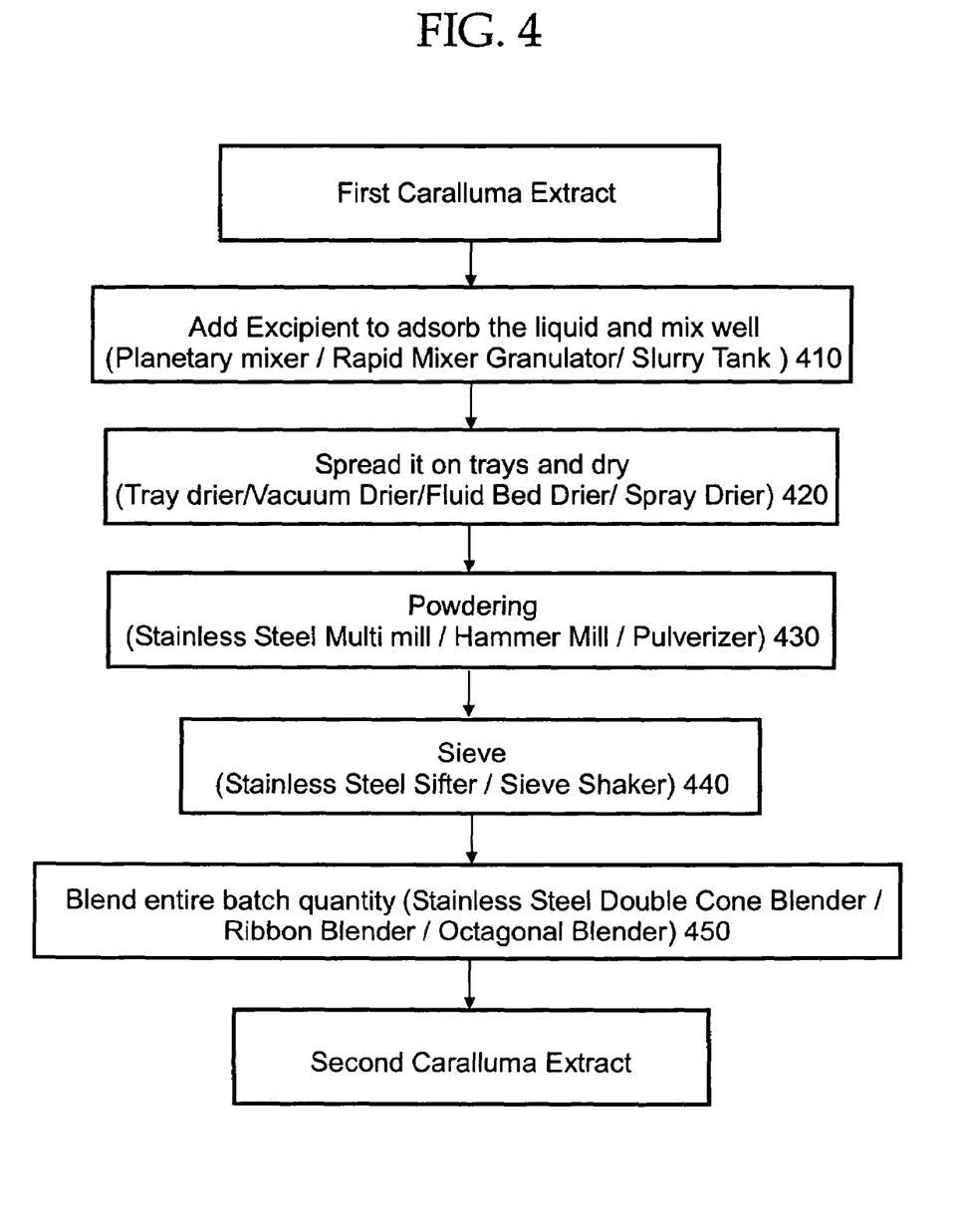
FIG. 4 shows one of the preferred processes for making the second *Caralluma* extract from the first *Caralluma* extract.

FIG. 1 shows an example of the process for making the first *Caralluma* extract from *Caralluma* plant matter. FIG. 2 shows an example of the process for making the second *Caralluma* extract from the first *Caralluma* extract. FIG. 3 shows one of the preferred processes for making the first *Caralluma* extract from *Caralluma* plant matter. FIG. 4 shows one of the preferred processes for making the second *Caralluma* extract from the first *Caralluma* extract.

The first step 110 comprises one or more optional pretreatment operations such as washing, cleaning, soaking, drying, cutting, chopping, blanching, and others, if necessary.

The plant material is preferably extracted as a powder. Thus, if the plant material is in large pieces, a cutting/chopping operation would be desirable to reduce it to a smaller size so that it can be ground to the desired mesh size for the extraction operation. Reducing the plant material size provides better contact during extraction and consequently faster extraction and also better heat transfer and uniformity of bed temperature in the extractor. Very fine plant material may tend to form lumps during extraction reducing the solid-liquid contact.

The crushing and/or grinding 120 of the raw plant material or the plant material obtained from the pretreatment is also optional. In this application, the term "crushing" includes crushing or grinding, or both. A number of grinding apparatus/equipments are available and are within the scope of the invention. A swing hammer mill is preferably used. If the plant material is in pieces rather than a powder, larger equipment is required for the same batch size, and a larger amount of solvent (or mixture) would also be necessary per batch. The batch times would also be correspondingly higher. The preferred size of the material-in-process after grinding is −10 BSS to +80 BSS. The extraction step 130 may be carried out by any of the several known methods such as batch, continuous, counter-current, series arrangement, parallel arrangement and others, by combinations of one or more of these, by hybrid schemes formed by fusing one or more of the methods.

One preferred example of the extraction method is of semi-parallel batch extraction with semi-countercurrent solvent feed. For instance, where a batch of plant material undergoes three separate extraction operations, a plurality of extractors are used. The three operations are referred to herein as "E1", "E2" and "E3". The solvent feed in the operation "E1" is not pure solvent but the somewhat weak extract obtained from the operation E3 of extraction. The solvent feed charged in the operations "E2" and "E3" is substantially pure solvent, which may be either fresh solvent or recovered solvent. The "A", "B" and "C" refer to the extracts (solutions) obtained in the operations, E1, E2 and E3, respectively. In the extraction step 130, undesirable non-glycoside components of *Caralluma* are also extracted, such as the tannins, pectins and resins that would affect the purity and storage properties of the product and that have side effects on the subjects treated with *Caralluma* glycoside products or *Caralluma* extracts.

Numerous combinations of the extraction methods, extraction schemes and solvent feed systems are possible. The choice of the extraction method may be governed by process economics factors such as solvent costs and availability, solvent recovery costs, batch times, energy costs for the heating of extractor contents, capital costs of various types of extraction equipment and others. Such factors vary from region to region and location to location. A wide range of extraction equipment is available. The choice is usually made on cost considerations and with the idea of keeping the batch times to the minimum. One preferred example of the extractor equipment is a jacketed stainless steel extractor.

The selection of the solvent is important. In view of the problems recognized by the inventors, a solvent should offer a good rate of extraction at low temperature and possess low solubility for the resins and also for the tannins and pectins. The rate of solubility of resins, tannins and pectins should also be as low as possible at the conditions adopted for extraction. That is, it is important to optimize a solvent and conditions of extraction (e.g., temperature and duration of extraction) so that the dissolution of the resinous matter is so reduced as to eliminate the necessity of the optional resin removal step and the entire concentration can be carried out in the first stage of concentration.

The present inventors have investigated a number of solvents for the extraction such as for example, acetone, iso-propyl alcohol, ethylene dichloride, n-hexane, n-butanol, water, methanol, ethanol, aq. methanol and aq. ethanol in view of the above factors.

100% methanol gives a poor yield of glycosides and extracts a large amount of resinous matter. This pushes up the solvent costs and solvent recovery costs of resin extraction. Similar results are obtained with methanol of 40% to 100% strength. The best yield of glycosides with a particular batch time is found to be with 20%–40% methanol. But the resin extraction is still high. Because of the resin extraction, the product gets sticky and hygroscopic. Accordingly, a resin removal operation is preferably performed. For example, when methanol is used as a solvent for extraction, n-hexane can be used for resin removal.

Use of ethylene dichloride as solvent without resin removal gives a sticky and hygroscopic *Caralluma* extract product. If resin removing solvent such as high strength aq. ethanol is used, the product is better but the yield of glycosides with ethylene dichloride is low compared to the use of 30% aq. ethanol where other parameters are substantially the same. The solvent costs and solvent recovery costs are high for both the extracting solvent and for the resin dissolving solvent.

Use of iso-propyl alcohol as solvent gave a good yield of glycosides. n-Hexane was used as the resin removing solvent. When iso-propyl alcohol was used, the *Caralluma* extract product was found to be of acceptable quality. However, iso-propyl alcohol is a costly solvent.

If water is used as a solvent with the resin dissolving solvent of n-butanol, the yield as well as the product quality is poor. In addition, n-butanol is an expensive solvent.

Costwise, ethanol is preferable to other solvents. Aqueous ethanol may give a good yield of glycosides. It is observed that, at higher strengths, the aqueous ethanol tends to extract more resin than at lower strengths, and that, at lower strengths, it tends to pick up more of the tannins and pectins than at higher strengths. Accordingly, the optimization of the concentration is important. It is preferred that the ethanol is of 10%–85% strength. It is also preferred that the ethanol concentration is 20%–40% by volume to get a good yield of glycosides.

Various solvent mixtures were investigated by these inventors such as mixtures of n-butanol, ethyl acetate and ethylene dichloride with ethanol, methanol, aq. ethanol, aq. methanol and others. The yields and the product quality were good. The cost was the constraint as n-butanol, ethylene dichloride and ethyl acetate are expensive solvents.

While the extraction at the higher temperature tends to keep the batch times shorter, the decomposition of glycosides increases with temperature. Therefore, the optimization of the temperature should be considered. Preferably, the extraction should be done in the temperature range of 70–80° C. when using aq. ethanol as solvent. More preferably, the extraction should be done in the temperature range of 70–75° C. because, where the extraction temperature is held at levels higher than 75° C., thermal decomposition of the glycosides occurs. Such high temperatures enhance the viscosity of the extract and increase the risk of decomposition in the concentration step.

Batch times can be controlled by controlling the temperature of extraction and the scheme of extraction adopted, solvent used, degree of agitation and others. With 20–40% aq. ethanol as solvent and extraction at 70–80° C. preferably the extraction is carried out in 3–4 stages, of which each batch time is about 5–8 hours. In these stages, either fresh solvent or weak solution(s) from other extractions is used.

The step 140 is a concentration step. Numerous methods of desolventification (solvent removal) including evaporation are available. It will be apparent to those skilled in the art that numerous methods for the concentration step 140 will also serve effectively.

The evaporated solvent may be recovered if desired.

The temperature of the evaporation is important. Where aq. ethanol is used, the evaporation is more preferably carried out at temperatures from 40° C. to 50° C. under vacuum.

A plurality of extract batches may come out from the extraction step 130. In the first stage of the concentration step 141, the concentration of the extract batch(es) may be carried out in a single operation or in a plurality of operations. Still further, where the plurality of batch(es) are present, the concentration operation may be carried out singly on each batch or on mixtures of one or more of the batches. Such combinations offer plant operational flexibility and scope for optimizing usage of plant.

For example, where the extract batches "A" and "B" come out from the extraction step 130, the extract batches "A" and "B" may undergo a first concentration operation singly to about one-tenth of the original volumes thereof. Subsequently, the batches "A" and "B" may be mixed and then concentrated further to about one fifth of the starting volume thereof. The concentration of the pregnane glycosides at the end of the mixed batch is preferably about 3–8% by wt. The preferred concentration is below the range at which any significant decomposition occurs.

The viscosity of an extract being concentrated goes up with increasing glycoside concentration. This problem is further compounded by the presence of the resinous matter in the extract. In fact, where glycoside concentration is above 3–8% by wt., overheating and/or charring may occur due to the high viscosity. Therefore, if the extract contains a large amount of resinous matter, it is advisable to terminate the first stage of concentration at this point and undertake the resin removal step 160 as it is the resin that is responsible for the high viscosities. After the resin removal, further concentration (i.e., the second stage of concentration 142) may be taken up. The first and second concentration stages 141, 142 may comprise a plurality of individual concentration operations. Accordingly, it is preferred that the resin removal step 160, if required, be carried out after the first stage of concentration 141 and before the second stage of concentration 142. The reduced volume of the partially concentrated solution(s) can reduce the requirement of the resin dissolving solvent.

The partially concentrated solution(s) at the end of the first concentration step 141 may include particulate impurities. An optional filtration operation 150 may be taken up at this stage to remove the particle impurities before sending the solution(s) to the second stage of concentration 142, or to the optional resin removal step 160 or before returning one or more solution(s) to the extractor(s) to reuse the solvent for the solvent feed for extraction step 130.

Whether or not the resin extraction is exercised depends on the resin content of the original plant material and how much the resin is extracted into the extract (i.e., solution). The latter depends on the nature of solvent and its concentration, and the conditions of extraction such as temperature and duration, agitation and others.

The resin removal 160 may be done as part of the pretreatment step 110. n-Hexane can be used as the resin dissolving solvent. Where substantially complete resin removal is achieved, the concentration step 140 can be done in one stage because the entire concentration even up to substantial total dryness could then be done in the first stage 141 without any noticeable decomposition. The resin removal 160 with n-hexane may be done with or without refluxing of the solvent. The drawback in this embodiment is that the consumption of n-hexane which is expensive is high.

The resin removal step 160 can also be done between the pretreatment step 110 and the crushing/grinding step 120. After the pretreatment step 110, the plant material is generally of a reduced size so that the requirement of the resin dissolving solvent is reduced.

The resin removal step 160 can be carried out after the crushing/grinding step 120. In this arrangement, there would be further reduction in the amount of solvent required because the crushing/grinding step 120 makes the material to be contacted with the solvent still finer. This has the effect of reducing the batch times for resin extraction.

The resin removal step 160 may be carried out also after the extraction step 130. If done at this stage, it would therefore be a liquid—liquid extraction operation. Contacting two liquids is a far more efficient operation and consequently the required amount of the solvent would be still less at this stage when all other conditions are equal. The number of batch times is also reduced.

Even if it is preferred that the resin removal step be carried out after the first stage of concentration 141 and before the second stage of concentration 142, different decisions as to when the resin removal step is carried out can be made on the basis of the cost and the availability of the resin solvent.

A number of resin dissolving solvents were tried in this invention, such as n-hexane, petroleum ether, benzene, toluene, diethyl ether, methylene dichloride and ethylene dichloride. The resin dissolving solvent can be selected on the basis of the cost of the process and on the cost and availability of the solvent and on considerations such as toxicity, ease of trace removal and others. In the present invention, n-hexane is preferred.

Generally speaking, if the resin content is desired to be reduced to the preferred values of not more than 0.5% w/w for the first *Caralluma* extract product and not more than 1.0% by wt for the second *Caralluma* extract product, it would be necessary to carry out the resin removal step 160. However, as mentioned hereinabove, this depends on the original resin content in the plant material and how much of it comes out in the extracts (solutions) during the extraction step.

The resin removal step 160 may include the step of washing the optionally filtered first concentrate, (the solution(s) obtained after the first concentration stage 141) with a suitable solvent that can dissolve the resinous matter contained in the filtrate. The washing (or leaching) may be carried our one or more times. The washing step is preferably a liquid—liquid extraction process and any of the various equipment known in the art for the purpose may be used.

The washed filtrate is subjected to a separation operation that results in two layers, one of which is a heavy layer having the glycosides in solution and the other of which is a light layer having the resin dissolving solvent. The separation can be carried out in any of the known equipment/apparatus available in the art for the purpose and adoption of any of them is within the scope of the invention.

The light layer having the resinous matter in solution is either discarded or subjected to a solvent recovery operation by any of the known means of solvent removal provided in the art. Preferably the solvent recovery is done by evaporation and condensation of the solvent.

The heavy layer contains the *Caralluma* glycosides and is subjected to the second concentration stage 142. Like the first concentration stage 141, the conventional concentration steps and their variations will be apparent to those skilled in the art. Preferably, the concentration 140 is done by evaporation of the solvent under vacuum using thin film evaporators.

The preferred temperature range for the evaporation is 40 to 50° C. when aq. ethanol is used as the extracting solvent. The evaporated solvent can be recovered by condensation. The selection of the method of solvent removal and of the equipment therefor is to a large extent based on cost factors.

The concentration is continued until the desired concentration of glycosides is reached. The heavy layer, that is, the concentrated solution at this stage constitutes the first *Caralluma* extract product of the invention.

As shown in FIG. 2, the second *Caralluma* extract product can be made from the first *Caralluma* extract.

The first *Caralluma* extract is first contacted with a suitable excipient 210. The contact may be carried out in any of the mixing apparatus/equipment such as, for example, planetary mixers, rapid mixers, granulators, slurry tanks and others that are found in the art. A number of suitable excipients are available in the art and may be used in the process of the invention. The preferred excipients are maltodextrin and magnesium carbonate.

Along with the excipient, the binders (binding agents) may be added if required or desired. Any of the known binding agents may be used in the process of the invention. Preferably, the binder is selected from the following, starch, gum Acacia, guar gum and polyvinyl pyrolidone. The mixing is continued until the adsorption of the first *Caralluma* extract on the excipient particles is completed, and the particles have a homogeneous coating of the glycosides and the binder, if used.

At this stage the material-in-process is removed and subjected to the drying step 220. The drying 220 is carried out by any of several methods of drying and by any of the many drying apparatus/equipment that are available in the art. Tray driers, fluid bed dryers, spray driers and vacuum driers are some of the drying apparatus/equipment available in the art. A tray drier and a spay dryer are preferred. The spray drying makes the product sticky and hygroscopic. For example, the blended material from the excipient step 110 may be thinly spread on the trays of the tray drier. This assists and accelerates the evaporation of the final traces of moisture, extraction solvent and the resin dissolving solvent. Accordingly, the excipient may be used for performing both an adsorption function and a function of facilitating further drying.

The dried material is basically the second *Caralluma* extract of the invention. Preferably, it is subjected to a grinding/milling (powdering) operation 230 to obtain a fine powder. The conventional equipment/apparatus such as multi-millers, hammer mills and pulverizers can be used for the grinding/milling step 230.

The product from the grinding/milling step 230 is then sifted in any of the known sifting, equipment/apparatus such as, but not limited to, a sieve shaker or sifter 240.

The sifted material is then blended in a blending machine such as, but not limited to, double cone blender, a ribbon blender, or an octagonal blender 250.

The output from the blending step 250 is the second *Caralluma* extract of the invention in a powder form.

In order to provide a clearer understanding of the invention and without limitation to the scope thereof, some examples will now be described and illustrated in FIGS. 3 and 4.

EXAMPLE 1

The aerial parts of *Caralluma fimbriata* plant were collected and dried in open-air under a shade 310. The dried material was ground in a swing hammer mill 320. For the extraction step 330, about 500 kgs. of this dry powder material was charged to an extractor. The extractor includes a stainless steel vessel of about 5,000 liters capacity provided with an agitator system and a surrounding jacket for steam heating. About 2,000 liters of about 30% aq. ethanol solvent was charged into the extractor. The solvent charged was formed by mixing about 600 liters of rectified spirit with about 1400 liters of water. The extractor contents were maintained at about 70–75° C. by heating with steam and the extraction was carried out for about six hours. This extract is referred to as "A". The volume of extract "A" was about 1,500 L.

The residue in the extractor comprising the partly-extracted *Caralluma* plant material was subjected to a second extraction (leaching) operation. About 2,000 liters of about 30% aq. ethanol was charged into the extractor and the extraction carried out at about 70–75° C. The extract was taken out of the extractor. The quantity of extract obtained was about 1,500 L. This extract is referred to as "B".

The plant residue in the extractor, comprising the twice-extracted *Caralluma* matter was subjected to the third extraction. About 1,500 L of about 30% aq. ethanol solvent was charged into the reactor (extractor) to yield about 1,500 L of extract at the end of the extraction operation which was carried out at about 70–75° C. This extract is referred to as "C".

For the first concentration step 341, the extracts "A" and "B" were both separately concentrated in concentrators down to a volume of about 150 L each. The extract "C" was used as solvent charge (solvent feed) for the first stage extraction of the next batch of *Caralluma* plant material. In this example, the solvent charge in the first extraction is solute-free aq. ethanol of about 30% strength. In the normal course, the solvent charge to the first extraction would be the "C" extract obtained from another batch. But being a freshly commenced extraction operation, the "C" extract was yet to become available and hence solute-free solvent was used.

At this stage, the concentrated extracts "A" and "B" are combined giving about 300 L of material (the step 344). This was filtered in a stainless steel Nutsche type Filter using Hyflosupercel as filter aid (the step 350). The filter bed was washed with about 50 L of about 30% aq. ethanol.

The filtrate contains the glycosides. About 300 L of n-hexane is added to the glycosides solution to dissolve out and remove the resinous matter therein (the step 360). After allowing a period of time for the hexane to dissolve the resinous matter the material-in-process was subjected to a separation operation 370 resulting in the separation of a light hexane-rich layer and the heavier glycoside solution. The hexane-rich layer was sent for hexane recovery while the glycoside solution layer was subjected to another treatment with n-hexane. Again about 300 L of hexane was used. The separation procedure was repeated giving the two layers out of which the lighter hexane layer was sent for hexane recovery and the heavier glycoside layer was sent for the second concentration step 342 where concentration was carried out in a thin film evaporator at about 45° C. and under a vacuum of less than 20 mm. of Hg. The concentrated material constituted the first *Caralluma* extract product. The above procedure was carried out five times to check whether the yields are reproducible. The amount of product obtained ranged between 55–65 kgs. The composition/analysis of the product obtained is given hereinbelow.

TABLE 5

Product: First *Caralluma* Extract
(From *Caralluma fimbriata*)

| Test Parameters | Specification | Actual Values |
| --- | --- | --- |
| Appearance | Brown to dark brown liquid | Complies |
| Solubility in water | Soluble | Soluble |
| Total dissolved Solids | 65% minimum w/w | 71% w/w |
| Total Bitters | 1.5% minimum w/w | 2% w/w |
| Total Saponin Glycosides | 5% minimum w/w | 7% w/w |
| Total Pregnane Glycosides | Above 15% w/w | 19.6% w/w |
| Resinous matters | Not more than 0.5% w/w | 0.05% w/w |
| Total microbial count | 5,000 cfu/gram max | 25 cfu/g |
| E. coli & Salmonella | Absent | Absent |
| Coliforms | Absent | Absent |
| P. Aeruginosa | Absent | Absent |
| S. Aureus | Absent | Absent |
| Heavy metals | 10 PPM maximum | Complies |

EXAMPLE 2

The solid type *Caralluma* extract product of the invention was prepared starting with the product of Example 1.

About 60 kgs. of the product obtained in Example 1 was mixed with the required quantity of maltodextrin, starch and gum acacia in a mixer and blended for about 30 minutes to get a homogeneous mass (the step 410).

The homogeneous mass was dried in a tray drier. The material was spread in a thin layer over the stainless steel trays of the drier and dried at a temperature of about 60° C. (the step 420).

The dried product from the foregoing step was powdered by, for example, a micropulverizer (the step 430) and then sifted in an S.S. Sifter to a particle size of about 40–80 mesh (the step 440). The sifted material was blended in a double cone blender for about one hour to get a homogeneous powder (the step 450).

The homogeneous powder was the second *Caralluma* extract product of the invention. The abovementioned procedure was repeated five times. The analysis range of the product obtained is given hereinbelow.

TABLE 6

Product: Second *Caralluma* Extract
(Standardized) (from *Caralluma fimbriata*)

| Test Parameters | Specification | Actual Values |
| --- | --- | --- |
| Appearance | Brown to dark brown liquid | Complies |
| Solubility in water | 75% minimum w/w | 97.0% w/w |
| Loss on Drying | 10% maximum w/w | 2.8% w/w |
| Total Bitters | 3% minimum w/w | 6.3% w/w |
| Total Saponin Glycosides | 10% minimum w/w | 17.8% w/w |
| Total Pregnane Glycosides | Above 30% w/w | 55.2% w/w |
| Resinous matters | Not more than 1% w/w | 0.15% w/w |
| Total microbial count | 5,000 cfu/gram max | 25 cfu/g |
| E. coli & Salmonella | Absent | Absent |
| Coliforms | Absent | Absent |
| P. Aeruginosa | Absent | Absent |
| S. Aureus | Absent | Absent |
| Heavy metals | 10 PPM maximum | Complies |

EXAMPLE 3

The same steps as outlined in the embodiment 2 were followed with the following differences. In Example 3, drying was conducted in a spray drier instead of a tray drier, and the homogeneous mass was dissolved in water as is required for feeding to a spray drier. The minimum quantity of water was used.

The spray dried *Caralluma* extract was found to be finer and more uniform in size and consequently it was not necessary to carry out the optional steps of powdering and sifting.

EXAMPLE 4

100% methanol was used as solvent with the resin dissolving solvent, n-hexane, to make the *Caralluma* extract starting with *Caralluma* plant material. The yield of glycosides was relatively low in comparison to the use of 30% aq. ethanol as in embodiment 1. n-Hexane consumption was high because of the higher amount of the resins extracted out by 100% methanol.

Methanol solvents of strengths 60%, 70%, 80% and 90% were also used. The observations of the inventors for these methanol concentrations are generally as for 100% methanol.

EXAMPLE 5

Aqueous methanol of 30% strength was used. The yield of glycosides was better than for the higher strengths. The yield is optimum at around 30% strength of methanol and is comparable to that for 30% aq. ethanol under comparable conditions. The product was the first *Caralluma* extract and the resin dissolving solvent used was n-hexane. A tray drier was used for drying.

EXAMPLE 6

Extraction was done with ethylene dichloride as solvent to produce the second *Caralluma* extract. The optional resin removal step was carried out for which n-hexane was used. Adsorption was done on maltodextrin. The product was found to be hygroscopic. The glycoside yield was lower than with 30% aq. ethanol solvent under similar conditions.

EXAMPLE 7

Aqueous methanol of 30% strength was used as the extraction solvent and n-hexane was used for resin removal. The product was the second *Caralluma* extract. Spray drying was adopted. The yield was equivalent to that of 30% aq. ethanol under comparable conditions. The product was hygroscopic.

Although the present invention has been described in considerable detail with reference to certain preferred versions thereof, other versions are possible. Therefore, the spirit and scope of the appended claims should not be limited to the description of the preferred versions contained herein.

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made. It should be appreciated that the scope of this invention is not limited to the detailed description of the invention hereinabove, which is intended merely to be illustrative, but rather comprehends the subject matter defined by the following claims.

What is claimed is:

1. A process for obtaining a *Caralluma* extract, comprising the steps of:
   providing a *Caralluma* plant material;
   extracting the *Caralluma* plant material by using a first solvent to obtain a solution;
   removing resinous material in the *Caralluma* plant material; and
   concentrating the solution to obtain the *Caralluma* extract.

2. The process of claim 1, wherein said *Caralluma* plant material is selected from the group consisting of the *Caralluma* species of *fimbriata, attenuata, tuberculata, adscendens*, and *indica*.

3. The process of claim 1, wherein said *Caralluma* plant material is selected from the group consisting of the *Caralluma* species of *stalagmifera, umbellata, lasiantha* and *edulis*.

4. The process of claim 1, further comprising the step of:
   pretreating the *Caralluma* plant material by at least one operation selected from the group consisting of washing, cleaning, soaking, drying, cutting, chopping, blanching, crushing and grinding the *Caralluma* plant material.

5. The process of claim 4, wherein the step of removing resinous material is performed between said pretreatment step and said extraction step.

6. The process of claim 4, wherein the step of removing resinous material is performed during said pretreatment step.

7. The process of claim 1, wherein said extraction step further comprises the step of extracting the *Caralluma* plant material by using said solution.

8. The process of claim 1, wherein said first solvent is selected from the group consisting of methanol, ethanol, aqueous methanol, aqueous ethanol, i-propyl alcohol, n-butanol, water, and ethylene dichloride.

9. The process of claim 1, wherein said first solvent is aqueous ethanol.

10. The process of claim 9, wherein said aqueous ethanol is about 10–80% v/v.

11. The process of claim 9, wherein said aqueous ethanol is about 20 to 40% v/v.

12. The process of claim 9, wherein said extraction step is carried out at temperature ranging from 70 to 75° C.

13. The process of claim 9, wherein said concentration step is carried out at temperature ranging from 40 to 50° C. under vacuum.

14. The process of claim 1, wherein said removal step is carried out after said extraction step.

15. The process of claim 1, wherein said removal step comprises using a second solvent selected from the group consisting of n-hexane, diethyl ether, ethylene dichloride, petroleum ether, benzene, toluene and methylene dichloride.

16. The process of claim 15, wherein said second solvent is n-hexane.

17. The process of claim 1, wherein said concentration step comprises concentrating the solution by evaporation.

18. The process of claim 17, further comprising recovering the first solvent evaporated by said evaporation.

19. The process of claim 1, wherein said concentration step comprises the steps of:
   first concentrating the solution; and
   second concentrating the first concentrated solution.

20. The process of claim 19, wherein, after the first concentrating step, a concentration of pregnane glycosides is about 3–8% w/w.

21. The process of claim 19, wherein the step of removing resinous material is performed after said first concentration step.

22. The process of claim 21, further comprising the step of, between said removal step and the second concentration step, filtrating the first concentrated solution to remove impurities.

23. The process of claim 22, wherein said removal step comprises the steps of:
    washing the filtered first concentrate with a second solvent; and
    separating the resinous material from the washed first concentrate.

24. The process of claim 19, further comprising the step of, before said second concentration step, filtrating the first concentrated solution to remove impurities.

25. The process of claim 24, wherein the step of removing resinous material is performed between said filtration step and the second concentration step.

26. The process of claim 1, further comprising the steps of:
    adding excipient to absorb liquid from the concentrated *Caralluma* extract; and
    after the adding step, drying the *Caralluma* extract to further remove liquid from the *Caralluma* extract.

27. The process of claim 26, wherein said excipient is selected from the group consisting of maltodextrin and magnesium carbonate.

28. The process of claim 26, further comprising adding binding agents.

29. The process of claim 28, wherein said binding agents are selected from the group consisting of starch, gum acacia, guar gum and polyvinyl pyrolidone.

30. The process of claim 26, wherein said drying step is performed by using a dryer selected from the group consisting of a tray dryer, a fluid bed dryer, a spray dryer, and a vacuum dryer.

31. The process of claim 26, further comprising the step of powdering the dried *Caralluma* extract.

32. The process of claim 31, further comprising the step of sifting the powdered *Caralluma* extract and subsequently blending the sifted *Caralluma* extract.

33. The process of claim 32, wherein said powdering step is performed by using a multi-miller, a hammer mill or a pulverizer.

34. A process for obtaining a first *Caralluma* extract, comprising the steps of:
    providing a *Caralluma* plant material;
    optionally pretreating said *Caralluma* plant material;
    optionally crushing or grinding of said *Caralluma* plant material;
    extracting the *Caralluma* plant material by using a first solvent to obtain a solution;
    removing resinous material after at least one of the providing step, the pretreating step, the crushing or grinding step, and the extracting step; and
    concentrating the solution to obtain the first *Caralluma* extract having not more than 0.5% w/w of the resinous material.

35. A process for obtaining a second *Caralluma* extract, comprising the steps of:
    providing a *Caralluma* plant material;
    optionally pretreating said *Caralluma* plant material;
    optionally crushing or grinding of said *Caralluma* plant material;
    extracting the *Caralluma* plant material by using a first solvent to obtain a solution; and
    concentrating the solution to obtain a first *Caralluma* extract;
    optionally removing resinous material after at least one of the providing step, the pretreating step, the crushing or grinding step, the extracting step, and the concentrating step;
    adding excipient to absorb liquid from the first *Caralluma* extract;
    drying the first *Caralluma* extract to obtain the second *Caralluma* extract having not more than 1% w/w of the resinous material;
    optionally powdering the dried second *Caralluma* extract;
    optionally sieving the powdered second *Caralluma* extract; and
    optionally blending the second *Caralluma* extract.

36. The process of claim 35, wherein said extraction step is carried out at temperature ranging from 70 to 75° C.

37. A process for obtaining a *Caralluma* extract, comprising the steps of:
    providing a *Caralluma* plant material;
    extracting the *Caralluma* plant material by using a first solvent to obtain a solution including not more than 8% w/w of pregnane glycosides; and
    concentrating the solution to obtain the *Caralluma* extract.

38. The process of claim 37, wherein said *Caralluma* plant material is selected from the group consisting of the *Caralluma* species of *fimbriata, attenuata, tuberculata, adscendens,* and *indica*.

39. The process of claim 37, wherein said *Caralluma* plant material is selected from the group consisting of the *Caralluma* species of *stalagmifera, umbellata, lasiantha* and *edulis*.

40. The process of claim 37, further comprising the step of:
    pretreating the *Caralluma* plant material by at least one operation selected from the group consisting of washing, cleaning, soaking, drying, cutting, chopping, blanching, crushing and grinding the *Caralluma* plant material.

41. The process of claim 40, further comprising the step of, between said pretreatment step and said extraction step, removing resinous material.

42. The process of claim 40, wherein said pretreatment step-further comprises removing resinous material.

43. The process of claim 37, wherein said extraction step further comprises the step of extracting the *Caralluma* plant material by using said solution.

44. The process of claim 37, wherein said first solvent is selected from the group consisting of methanol, ethanol, aqueous methanol, aqueous ethanol, i-propyl alcohol, n-butanol, water, and ethylene dichloride.

45. The process of claim 37, wherein said first solvent is aqueous ethanol.

46. The process of claim 45, wherein said aqueous ethanol is about 10–80% v/v.

47. The process of claim 45, wherein said aqueous ethanol is about 20 to 40% v/v.

48. The process of claim 45, wherein said extraction step is carried out at temperature ranging from 70 to 75° C.

49. The process of claim 45, wherein said concentration step is carried out at temperature ranging from 40 to 50° C. under vacuum.

50. The process of claim 37, further comprising the step of removing resinous material.

51. The process of claim 50, wherein said removal step is carried out after said extraction step.

52. The process of claim 51, wherein said removal step further comprises using a second solvent selected from the group consisting of n-hexane, diethyl ether, ethylene dichloride, petroleum ether, benzene, toluene and methylene dichloride.

53. The process of claim 52, wherein said second solvent is n-hexane.

54. The process of claim 37, wherein said concentration step comprises concentrating the solution by evaporation.

55. The process of claim 54, further comprising recovering the first solvent evaporated by said evaporation.

56. The process of claim 37, wherein said concentration step comprises the steps of:
first concentrating the solution; and
second concentrating the first concentrated solution.

57. The process of claim 56, wherein, after the first concentrating step, a concentration of the pregnane glycosides is about 3–8% w/w.

58. The process of claim 56, further comprising the step of removing resinous material from the first concentrated solution, before said second concentration step.

59. The process of claim 58, further comprising the step of filtrating the first concentrated solution to remove impurities, between said removal step and the second concentration step.

60. The process of claim 59, wherein said removal step comprises the steps of:
washing the filtered first concentrate with a second solvent; and
separating the resinous material from the washed first concentrate.

61. The process of claim 56, further comprising the step of filtrating the first concentrated solution to remove impurities, before said second concentration step.

62. The process of claim 61, further comprising the step of removing resinous material from the concentrated solution, between said filtration step and the second concentration step.

63. The process of claim 37, further comprising the steps of:
adding excipient to absorb liquid from the concentrated *Caralluma* extract; and
after the adding step, drying the *Caralluma* extract to further remove liquid from the *Caralluma* extract.

64. The process of claim 63, wherein said excipient is selected from the group consisting of maltodextrin and magnesium carbonate.

65. The process of claim 63, further comprising the step of adding binding agents.

66. The process of claim 65, wherein said binding agents are selected from the group consisting of starch, gum acacia, guar gum and polyvinyl pyrolidone.

67. The process of claim 63, wherein said drying step is performed by using a dryer selected from the group consisting of a tray dryer, a fluid bed dryer, a spray dryer, and a vacuum dryer.

68. The process of claim 63, further comprising the step of powdering the dried *Caralluma* extract.

69. The process of claim 68, further comprising the step of sifting the powdered *Caralluma* extract and subsequently blending the sifted *Caralluma* extract.

70. The process of claim 37, wherein said extraction step is carried out at temperature ranging from 70 to 75° C.

71. A process for obtaining a *Caralluma* extract, comprising the steps of:
providing a *Caralluma* plant material;
extracting the *Caralluma* plant material by using a first solvent to obtain a solution at temperature not more than about 75° C.; and
concentrating the solution to obtain the *Caralluma* extract.

* * * * *

UNITED STATES PATENT AND TRADEMARK OFFICE
CERTIFICATE OF CORRECTION

PATENT NO. : 7,060,308 B2
APPLICATION NO. : 10/837613
DATED : June 13, 2006
INVENTOR(S) : Ramaswamy Rajendran et al.

It is certified that error appears in the above-identified patent and that said Letters Patent is hereby corrected as shown below:

On title page
Please insert the following:

(30) Foreign Application Priority Data

27 April, 2004 (IN) 384/CHE/2004.

Signed and Sealed this

Fifteenth Day of August, 2006

JON W. DUDAS
*Director of the United States Patent and Trademark Office*